United States Patent [19]

Albright et al.

[11] Patent Number: 5,277,875

[45] Date of Patent: Jan. 11, 1994

[54] SELF-CONTAINED STERILIZER WITH DUTY-CYCLE HEATER

[75] Inventors: Donald W. Albright, Rochester; Raymond J. Miller, Penfield, both of N.Y.

[73] Assignee: MDT Corporation, Torrance, Calif.

[21] Appl. No.: 412,411

[22] Filed: Sep. 26, 1989

[51] Int. Cl.[5] .................... G05D 7/00; G05D 23/00; A61L 2/00

[52] U.S. Cl. .................... 422/109; 422/110; 422/114; 422/116; 422/295; 422/299

[58] Field of Search ............ 422/26, 27, 30, 108, 422/109, 110, 114, 116, 119, 295, 298, 299

[56] References Cited

U.S. PATENT DOCUMENTS

| | | | |
|---|---|---|---|
| 3,431,065 | 4/1965 | Schipanski | 422/116 |
| 3,687,612 | 8/1972 | Earnst | 422/27 |
| 4,164,538 | 8/1979 | Young et al. | 422/26 |
| 4,324,762 | 4/1982 | Redikultsev et al. | 422/106 |
| 4,335,071 | 6/1982 | Thornton | 422/26 |
| 4,447,399 | 5/1984 | Runnells et al. | 422/113 |
| 4,497,773 | 2/1985 | Kuelzow et al. | 422/26 |
| 4,687,635 | 8/1987 | Kaehler et al. | 422/26 |
| 4,865,814 | 9/1989 | Childress | 422/108 |
| 4,909,988 | 3/1990 | Childers et al. | 422/26 |
| 4,944,919 | 7/1990 | Powell | 422/26 |

FOREIGN PATENT DOCUMENTS 2052800 1/1981 United Kingdom .................. 422/27

OTHER PUBLICATIONS

Childers, et al., "Utility Efficient Electric Steam Sterilizer", Mar. 1986.

Primary Examiner—Robert J. Warden
Assistant Examiner—Theresa A. Trembley
Attorney, Agent, or Firm—Trask, Britt & Rossa

[57] ABSTRACT

A microprocessor-controlled, self-contained steam sterilizer is disclosed. Once the steam exposure phase is complete in the sterilizer, the microprocessor is programmed to operate the vaporizing heater in a low-power duty cycle to utilize the vaporizing heater as a drying heater in a lower power operating mode to effect a drying phase.

13 Claims, 2 Drawing Sheets

5,277,875

SELF-CONTAINED STERILIZER WITH DUTY-CYCLE HEATER

BACKGROUND OF THE INVENTION

Field:

The present invention is directed toward a sterilizer with an improved drying phase, and particularly toward one in which a high-capacity vaporizing heater is operated subsequent to an exposure phase in a low-power mode to effect drying of a load.

State of the Art

Portable or self-contained sterilizers typically include an internal reservoir of water and a heater mounted at the bottom of the pressure vessel. The reservoir is typically filled with distilled water. A fixed amount or "charge" of water from the reservoir is dispensed into the pressure chamber for each sterilizing cycle. This charge of water fills the bottom of the chamber above an area heated by an electrical heating element. Water vaporization elements are necessarily of large capacity, typically from about 800 Watts to about 1800 Watts. The article to be sterilized, or "load," is subjected to an environment of pressurized, saturated steam. Sterilizers of this type are sometimes referred to as "table top" or "unplumbed" sterilizers.

After completion of the steam exposure phase of operation, it may be necessary to subject the load to a "drying phase," in which the chamber door is left ajar and dry heat is applied to the chamber. The water vaporizing element provides too much heat for this purpose. A low wattage heater (typically of fixed wattage between about 100 Watts to about 500 Watts) is thus conventionally mounted in the sterilizer. This low capacity heater is energized for a selected period of time to drive residual moisture from the load. The capacities of the vaporizing heater and the drying heater are selected on the basis of the size of the sterilizer vessel. The larger the vessel is, the higher the capacity for both the vaporizing heater and the drying heater. For example, a typical sterilizer may have a 1500 Watt vaporizing heater with a 150 Watt drying heater.

Such self-contained sterilizers, however, often do not provide adequate drying. Inadequate drying is particularly noticeable in the case of certain objects, such as sterilized instruments and wrapped instrument packs. During the sterilization process, steam typically penetrates the wrapped loads and condenses on instruments. After sterilization, this residual moisture must be removed or driven out of the packs to effect a complete sterilization.

Currently used drying systems also allow for inconsistent and incomplete results due to the many variables in the process. Such variables include, for example, how far the door is left open, AC line voltage, chamber temperature, the size and mass of the load, and air flow within the chamber. If a time period has elapsed between the exposure phase and the drying phase, the sterilizer, the load, and any condensed water may have cooled to room temperature. A low-wattage heater may be slow or ineffective in warming the load and the condensed water to a proper drying temperature.

There remains a need for a pressure chamber or sterilizer which provides for an improved drying phase and which eliminates the need for a separate low-power drying heater.

SUMMARY OF THE INVENTION

The present invention provides a sterilizer that includes a pressure vessel with an associated door. The pressure vessel is adapted to receive a sterilizable load and to contain the load within the interior of the vessel with the door closed, the door thereby adapted to seal the interior of the vessel. A reservoir is associated with the pressure vessel and is adapted to contain liquid. The liquid may be water or other sterilizing chemicals, or, for example, a solution of water mixed with a sterilizing agent. A fluid line links the reservoir with the interior of the pressure vessel. Valve means is associated with the fluid line for controlling the flow of fluid between the reservoir and the interior of the pressure vessel. A heater is associated with the pressure vessel and is capable of operation selectively in a high-power mode and in a low-power mode. The heater has sufficient capacity to vaporize liquid within the interior when the heater is operated in the high-power mode. Control means is operably associated with the heater and is adapted to operate the heater in its high-power mode during an exposure phase of operation and to thereafter operate the heater in its low-power mode during a drying phase of operation.

In a preferred embodiment, the control means includes a microprocessor programmed to operate said heater in a duty cycle to effect the low-power mode of the heater. In a highly preferred embodiment, the microprocessor is programmed to operate the heater in the duty cycle by repetitiously turning the heater on and off throughout the drying phase. Preferably, the microprocessor is programmed to turn the heater on and to turn the heater off each respectively a preselected percentage of time during the drying phase to achieve a preselected average drying power.

The microprocessor may be advantageously programmed to receive a user-selected time duration for the drying phase. The sterilizer preferably includes a temperature sensor associated with the vessel and communicatively linked with the microprocessor, the microprocessor being programmed to delay the timing of the drying phase until the temperature in the vessel is above a preselected control temperature. In a highly preferred embodiment, the vessel, reservoir, heater, and microprocessor are assembled as an integral, self-contained unit.

Sterilizers of the invention provide for an improved drying phase. Rather than using a separate low wattage heater for the drying phase, the vaporizing heater is operated after the exposure phase in a low-power mode to effect a drying phase. This arrangement improves the consistency, reliability, and effectiveness of drying compared to sterilizers which employ a drying heater separate from the vaporizing heater, which have heretofore been conventional in sterilizers of this type.

DETAILED DESCRIPTION OF THE ILLUSTRATED EMBODIMENT

Figure 1:
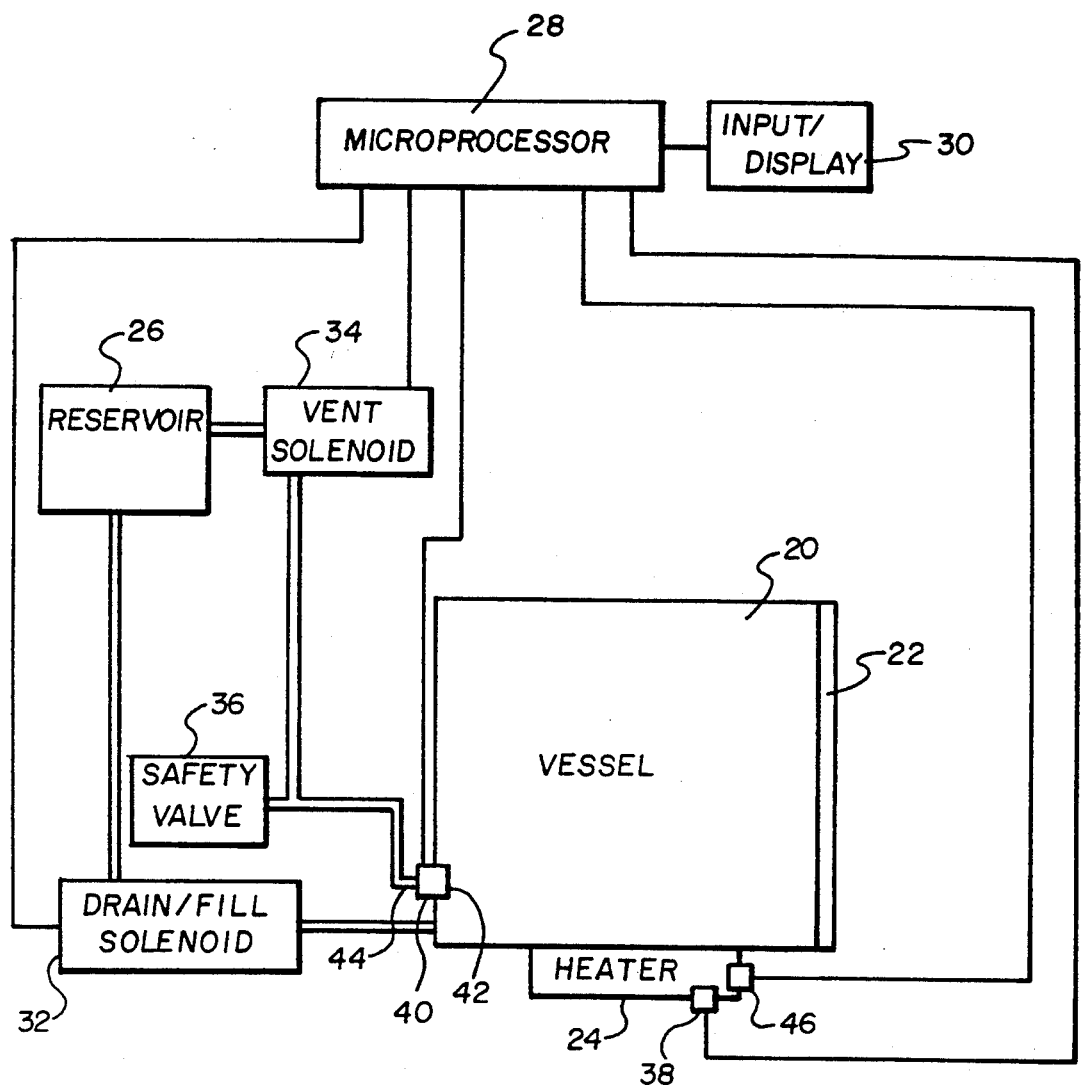
FIG. 1 is a schematic illustration of a sterilizer of the invention.

Referring to FIG. 1, the illustrated sterilizer includes a pressure vessel 20 having an associated door 22, a heater 24, a reservoir 26, a microprocessor 28, and an input/display 30. Also included in the sterilizer is a drain/fill solenoid valve 32, a vent solenoid valve 34, and a safety valve 36. Heater 24 is of sufficient power rating and selected for the size of the vessel (typically about 1500 Watts) to vaporize water within the interior of vessel 20 to thereby pressurize the interior of vessel 20 with saturated steam within a predetermined time period, typically no more than a few minutes.

In FIG. 1, electrical connections are represented by single connection lines and fluid connections are represented by double connection lines. A temperature sensor 38 is mounted on heater 38 as a safety device. A temperature sensor 40 is mounted in vessel 20 at the opening 42 of fluid line 44, which extends between vessel 20 and safety valve 36, as shown. Microprocessor 28 is electrically connected to drain/fill solenoid valve 32, to vent solenoid valve 34, to temperature sensor 38, to temperature sensor 40, and to switch 46, which operates heater 24. Switch 46 is a TRIAC, i.e., a bidirectional triode thyristor. A switch, alternate switch 46 may comprise a standard relay.

As shown, reservoir 26 is connected by fluid lines to drain/fill solenoid valve 32 and to vent solenoid valve 34. Drain/fill solenoid valve 32 is connected by a fluid line to vessel 20. Vent solenoid valve 34 is connected by fluid lines to safety valve 36 and to vessel 20. Vent port 42 for line 44 is located just above the selected water level to assure unobstructed air removal. Microprocessor 28 is programmed to control drain/fill solenoid valve 32, vent solenoid valve 34, and heater 24, by means of switch 46, to effect the appropriate sterilizing cycle and drying phase.

Microprocessor 28 is preferably a standard four bit microcontroller with I/0 expander. The programming of such microprocessors to harmonize with novel system designs such as disclosed herein is well known. It is also within contemplation to utilize a controller device of other known type which does not use a microprocessor in place of microprocessor 28. Duty cycles may be accomplished with conventional non-computerized electronics. However, in view of the current relative low cost, ease of programming, and versatility of microprocessors, the invention is described in this disclosure by reference to such devices. Input/display 30 may be a typical x-y matrix alphanumeric key board with an LCD or LED alphanumeric display for giving user prompts.

Figure 2:
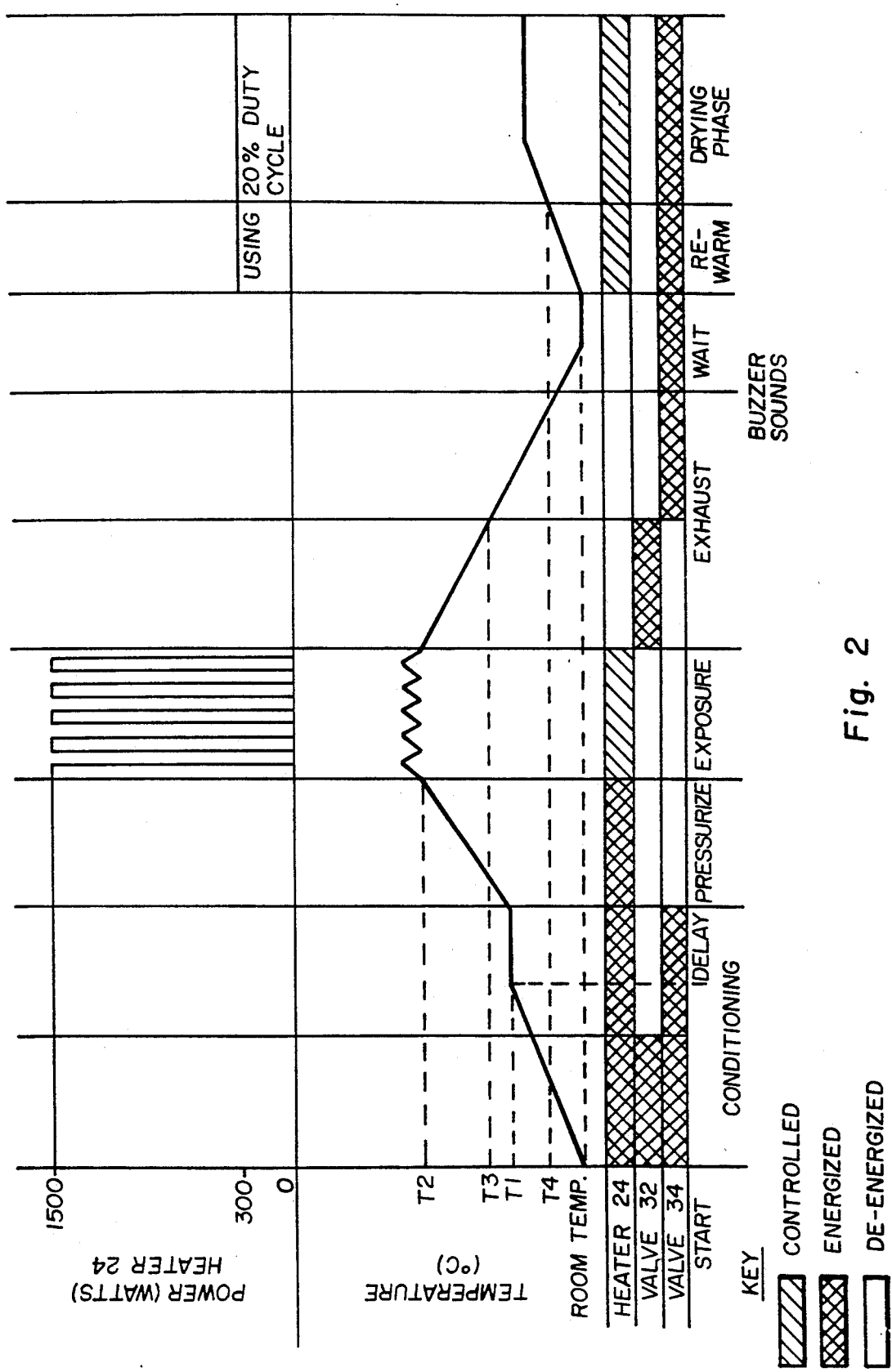
FIG. 2 is a graph of a typical sterilizing cycle and drying phase of a sterilizer of the invention.

FIG. 2 is a chart depicting various events as a function of time during a sterilizing cycle and a drying phase for a sterilizer of the invention. The upper portion of the chart depicts the power output of heater 24. The central portion depicts the temperature in vessel 20. The lower portion of the chart indicates the states of heater 24, drain/fill solenoid valve 32, and vent solenoid valve 34 during at various phases of the cycle.

In the lower part of the chart, the "key" indicates the possible states for heater 24, drain/fill solenoid valve 32, and vent solenoid valve 34. Slanted parallel lines indicate a controlled state for heater 24. "Controlled" for heater 24 means cycled on and off to achieve either a selected temperature (as in the exposure phase, described infra) or a selected average drying power (as in the drying phase, described infra). Criss-crossing lines indicate an energized condition. An "energized" state for heater 24 means that heater 24 is operated at full capacity (e.g. 1500 Watts). A "de-energized" state for heater 24 means that heater 24 is turned off.

An "energized" state for solenoid valve 32 or solenoid valve 34 means that the solenoid associated with its respective valve is energized to open the valve to thereby allow fluid flow. A "de-energized" state for valves 32 and 34 indicates that the respective solenoid is electrically disengaged to close the valve to thereby prohibit fluid flow. The states of heater 24, drain/fill solenoid valve 32, and vent solenoid valve 34 are controlled by microprocessor 28, based on the data received at input/display 30 and temperatures read at sensors 38 and 40.

An operator selects an appropriate cycle, including an appropriate temperature and time duration for the exposure phase, at input/display 30 to initiate the process. Based upon this selection, microprocessor 28 is programmed to effect the appropriate sterilizing cycle. The phases and other events of this cycle are marked horizontally across the bottom of the chart of FIG. 2. The temperature in vessel 20 may begin the cycle at room temperature. However, if the sterilizer has been recently used, the temperature in vessel 20 may be above room temperature. A "conditioning" begins when microprocessor 28 opens drain/fill solenoid valve 32 to fill the bottom of vessel 20 with a preselected quantity (charge) of water from reservoir 26. To prevent back pressure, vent solenoid valve 34 is also opened at the same time. To decrease cycle time, microprocessor 28 is programmed to turn heater 24 on during the filling of water to begin producing steam. Once the preselected quantity of water has been dispensed from reservoir 26, into the vessel 20, microprocessor 28 is programmed to close drain/fill solenoid valve 32.

Temperature sensor 40 senses the temperature of air and/or steam leaving vessel 20. Vent solenoid valve 34 is left open to allow steam produced by heater 24 to drive away dry air. Once microprocessor 28 reads a particular temperature T1 (for example 98° C.) at sensor 40, microprocessor 28 sets a preselected programmed delay (for example two minutes). After the delay, vent solenoid valve 34 is closed to allow a buildup of pressure in vessel 20.

Once valve 34 is closed, pressure builds during the phase marked "pressurize" in FIG. 2. The temperature also increases during this time. Temperature T2 is the exposure temperature for the sterilizer. This exposure temperature may be, for example, between 100° C. and 135° C.

Microprocessor 28 is programmed, once T2 is reached, to control heater 24 in an exposure phase. Microprocessor 28 reads the temperature in vessel 20 at sensor 40 and turns heater 24 on and off in a thermostat fashion to maintain the temperature in vessel 20 at the exposure temperature T2 within a preselected tolerance, which may be, for example, 1 or 2 degrees. Microprocessor 28 is programmed to maintain this exposure temperature for the operator selected exposure time between, for example, 3 to 99 minutes.

Microprocessor 28 is programmed, once the exposure phase is complete, to effect an exhaust phase. If the load is non liquid, microprocessor 28 opens drain/fill solenoid valve 32 immediately to exhaust any residual water and pressure in vessel 20 back into reservoir 26. A majority of the "charge" has typically not been vaporized, and must therefore be vented back to reservoir 26. When temperature T3 is reached, typically about 101° C., drain/fill solenoid valve 32 is closed and vent solenoid valve 34 is opened to complete the pressure exhaust phase. The vessel 20 pressure is thereby returned to atmospheric pressure.

Microprocessor 28 is programmed, once valve 20 has been opened, to give a prompt to the input/display 30 that the operator can then initiate the drying phase. Microprocessor 28 may also be linked to a light or buzzer to signal when the sterilization cycle is complete. At this time, the operator may open door 22 slightly and input at input/display 30 a command to begin the drying phase. Microprocessor 28 is programmed to ask the operator for a selected drying time. The operator then enters such drying time at input/display 30.

Microprocessor 28 is programmed to turn heater 24 on and off repetitiously by means of switch 46 thereby to effect a duty cycle of heater 24 at a preselected and preprogrammed average power output, which is lower than its maximum power output. For a 1178 cubic inch vessel and a 1500 Watt heater, it has been found that a 20% duty cycle is effective for drying of typical loads. Such a 20% duty cycle results in a 300 Watt average power output, or "average drying power." The average drying power may be selected on the basis of the size of the vessel and other features such as intended types of loads to be sterilized.

It is preferred that the average drying power be preprogrammed by the manufacturer, as opposed to being selectable by an operator. The manufacturer preferably chooses an average drying power considering, e.g., the size of the vessel, characteristics of typical loads, etc., to achieve effective drying without risk of over-heating, burning, or otherwise damaging loads.

In a model intended for use by experienced and trained operators, the average drying power of the heater may be user-selectable. In such a model, the microprocessor is programmed to receive a selected average drying power, such as, for example, 375 Watts. At this average power output, with a 1500 Watt heater, the microprocessor divides 375 by 1500 to derive a 25% on and 75% off duty cycle.

It is not uncommon, once the steam cycle is complete, for an operator to wait an extended period of time before he starts the drying phase. Such an optional waiting period is marked "wait" on the chart of FIG. 2. For example, an operator might place a load in the sterilizer and begin the sterilizing or steam cycle just before leaving for the day. In the morning when he returns, the sterilizer will be cold, i.e., room temperature, as shown in the "wait" period of FIG. 2. The drying phase remains to be done. In existing systems which utilize a fixed-wattage (e.g., a 100-150 Watt) drying heater, a drying phase initiated under these circumstances tends to be slow and ineffective. A conventional low wattage heater must work against the low temperature of the load and the water that has condensed on the load.

However, in the preferred embodiments of the claimed sterilizer, if microprocessor 28 reads a temperature in vessel below a specific control temperature T4, such as 35° C., microprocessor 28 operates heater 24 at its selected duty-cycle average drying power (e.g. 300 Watts) until the control temperature T4 is achieved. (See "rewarm" phase, FIG. 2.) Once the control temperature T4 is achieved, microprocessor 28 is programmed to begin the timing of the drying phase and to continue to operate heater 24 in its low-power duty-cycle mode for the preselected time duration of the drying phase. Suitable control temperatures T4 have been found to be between 35° C. and 75° C.

Sensor 38 is included as a safety feature, and senses the temperature of the heating element of heater 24. Microprocessor 28 reads this temperature. If the temperature is above a preselected value, microprocessor 28 shuts heater 24 off, regardless of the phase of the cycle being effected, and gives an indication that heater 24 has overheated at input/display 30. This preselected overheat temperature is chosen at a level to avoid damage to the sterilizer or to a load being sterilized.

While duty cycles involving a simple on and off cycle of the heater are currently preferred, a workable duty cycle may also be accomplished by programming the microprocessor to switch the heater between two levels of power output, in which the minimum power is not necessarily zero. Alternatively, electronic means may be provided to operate heater 24 at a constant low-power wattage, without resort to the use of a duty cycle. Switch 46 is a TRIAC and can be operated by microprocessor 28 to variably control at selected constant levels the power output of heater 24.

Reference herein to details of the illustrated embodiment is not intended to limit the scope of the appended claims, which themselves recite those features regarded as important to the invention.

We claim:

1. A sterilizer, comprising:
   a pressure vessel adapted to receive a sterilizable load and to contain said load within the interior of said pressure vessel, said pressure vessel having a door adapted to seal said interior;
   a reservoir operably associated with said pressure vessel and adapted to contain liquid, with a fluid line linking said reservoir with the interior of said pressure vessel;
   valve means operably associated with said fluid line for controlling the flow of fluid between said reservoir and the interior of said pressure vessel;
   a heater operably associated with said pressure vessel and capable of operation selectively in a high-power mode and in a low-power mode, said heater having sufficient capacity to convert liquid within said interior to vapor when said heater is operated in said high-power mode;
   temperature sensing means operably associated with said pressure vessel for sensing temperature of said pressure vessel; and
   control means operably associated with said heater and said temperature sensing means and adapted to operate said heater in said high-power mode during an exposure phase of operation and to thereafter operate said heater in said low-power mode during a drying phase of operation, and wherein during the exposure phase the control means turns the heater on and off in a thermostat fashion to maintain the temperature of said pressure vessel at a predetermined temperature within a preselected tolerance.

2. A sterilizer according to claim 1 wherein said control means includes a microprocessor programmed to effect said low-power mode of operation.

3. A sterilizer according to claim 2 wherein said microprocessor is programmed to operate said heater in said low-power mode of operation by repetitiously turning said heater on and off.

4. A sterilizer according to claim 3 wherein said microprocessor is programmed to turn said heater on and to turn said heater off respectively a preselected percentage of time during said drying phase thereby to operate said heater at a preselected average power output.

5. A sterilizer according to claim 2 wherein said microprocessor is programmed to receive a user-selected time duration for said drying phase.

6. A sterilizer according to claim 2, said microprocessor being further programmed to operate said heater to warm the interior of said pressure vessel if the temperature in said pressure vessel is below a predetermined control temperature subsequent to said exposure phase and to begin timing of said drying phase duration only when the temperature in said pressure vessel is above said control temperature.

7. A sterilizer according to claim 1 wherein said pressure vessel, said reservoir, said heater, and said control means are assembled together as an integral self-contained unit.

8. A self-contained sterilizer, comprising:
a pressure vessel adapted to receive a sterilizable load into its interior;
a door operably associated with said pressure vessel and adapted to operate between an open position and a closed position, said door sealing said interior in said closed position;
a reservoir operably associated with said pressure vessel and adapted to contain water;
a fluid line linking said reservoir with said interior;
valve means operably associated with said fluid line for controlling the flow of water between said reservoir and said interior;
a heater operably associated with said pressure vessel and capable of operation selectively in a high-power mode and in a low-power mode, said heater having sufficient capacity to convert water within said interior to steam when said heater is operated in said high-power mode;
temperature sensing means operably associated with said pressure vessel for sensing temperature of said pressure vessel; and
a microprocessor operably associated with said pressure vessel and communicatively linked with said valve means, the temperature sensing means, and said heater;
said microprocessor being adapted to effect a steam exposure phase by being programmed to:
open said valve means to dispense water from said reservoir into said interior,
close said valve means to fluid-tightly seal said interior, and
operate said heater in said high-power mode thereby to pressurize said interior with steam, the microprocessor turning the heater on and off in a thermostat fashion to maintain the temperature of said pressure vessel at a predetermined temperature within a preselected tolerance;
said microprocessor being further adapted to effect a drying phase subsequent to said steam exposure phase by being programmed to operate said heater in said low-power mode.

9. A self-contained sterilizer according to claim 8 wherein said microprocessor is programmed to operate said heater in a duty cycle to effect said low-power mode.

10. A self-contained sterilizer according to claim 9 wherein said microprocessor is programmed to operate said heater in said low-power operating mode by repetitiously turning said heater on and off.

11. A self-contained sterilizer according to claim 10 wherein said microprocessor is programmed to turn said heater on and to turn said heater off respectively a preselected percentage of time during said drying phase.

12. A self-contained sterilizer according to claim 8, said microprocessor being programmed to operate said heater to warm the interior of said pressure vessel if the temperature in said pressure vessel is below a predetermined control temperature subsequent to said steam exposure phase and to begin timing of said drying phase only when the temperature in said pressure vessel is above said control temperature.

13. A self-contained sterilizer according to claim 12 wherein said microprocessor is programmed to accept a user-selected time duration for said drying phase.

* * * * *